(12) United States Patent
Hansson et al.

(10) Patent No.: US 10,117,692 B2
(45) Date of Patent: Nov. 6, 2018

(54) FIXING MEANS FOR FIXATION OF BONE FRAGMENTS AT BONE FRACTURES

(71) Applicant: Swemac Innovation AB, Linköping (SE)

(72) Inventors: Henrik Hansson, Vreta Kloster (SE); Lars Oster, Lidköping (SE)

(73) Assignee: SWEMAC INNOVATION AB (SE)

( * ) Notice: Subject to any disclaimer, the term of this patent is extended or adjusted under 35 U.S.C. 154(b) by 621 days.

(21) Appl. No.: 14/434,763

(22) PCT Filed: Oct. 12, 2012

(86) PCT No.: PCT/SE2012/051096
§ 371 (c)(1),
(2) Date: Apr. 10, 2015

(87) PCT Pub. No.: WO2014/058367
PCT Pub. Date: Apr. 17, 2014

(65) Prior Publication Data
US 2015/0289915 A1    Oct. 15, 2015

(51) Int. Cl.
*A61B 17/84* (2006.01)
*A61B 17/72* (2006.01)
*A61B 17/86* (2006.01)

(52) U.S. Cl.
CPC .......... *A61B 17/846* (2013.01); *A61B 17/844* (2013.01); *A61B 17/8685* (2013.01);
(Continued)

(58) Field of Classification Search
CPC . A61B 17/8685; A61B 17/846; A61B 17/844; A61B 17/7266; A61B 2017/8655
(Continued)

(56) References Cited

U.S. PATENT DOCUMENTS 4,498,468 A    2/1985  Hansson
6,162,234 A   12/2000  Freedland et al.
(Continued)

FOREIGN PATENT DOCUMENTS

SE     433 166      5/1984
SE    1051333       7/2012
(Continued)

*Primary Examiner* — Olivia C Chang
(74) *Attorney, Agent, or Firm* — Tarolli, Sundheim, Covell & Tummino LLP

(57) ABSTRACT

A fixing means (1) for fixation of bone fragments at bone fractures comprises a sleeve (2) and at least one pin (9) which is provided in said sleeve and a front end portion (10) of which can be driven out and retracted through a side opening (8) in the sleeve such that said end portion can be brought to engage bone material in one of the bone fragments and retracted out of the bone material. For facilitating said driving and retraction, the pin (9) comprises a fixing member (9a) with said front end portion (10) and a driving and retraction member (9b) which is rotatably connected to the fixing member. The driving and retraction member (9b) is configured to, during rotation in a first direction relative to the fixing member (9a), displace the pin (9) in a forward direction relative to the sleeve (2) for driving the front end portion (10) of the pin out of the sleeve and into the bone material in said one bone fragment and, during rotation in a second, opposite direction relative to the fixing member, displace the pin in a backward direction relative to the sleeve for retracting the front end portion of the pin out of the bone material in said one bone fragment and into the sleeve.

21 Claims, 12 Drawing Sheets

Figure 2:
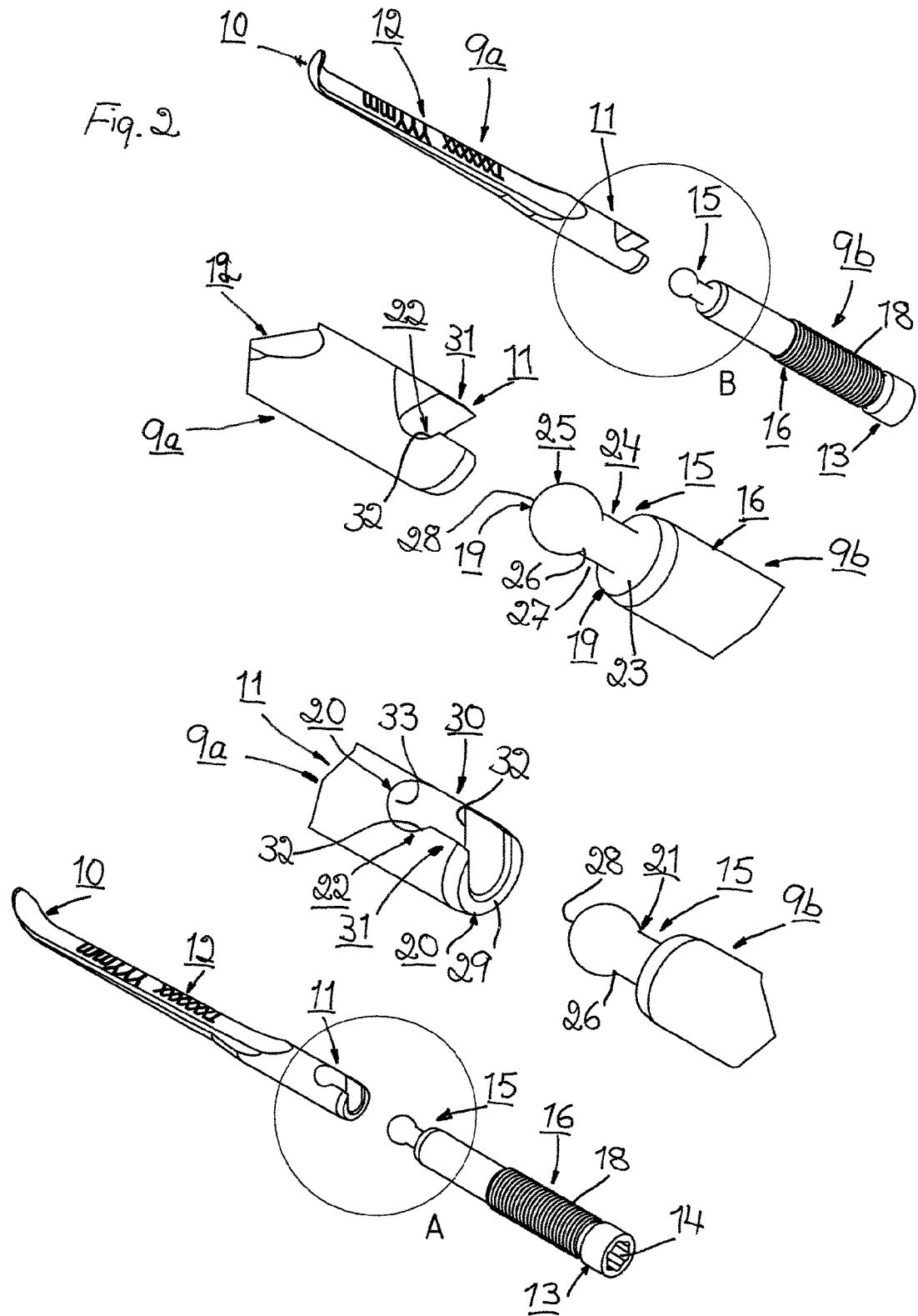

(52) U.S. Cl.
 CPC ......... *A61B 17/7266* (2013.01); *A61B 17/864* (2013.01); *A61B 2017/8655* (2013.01)

(58) Field of Classification Search
 USPC ........................................................ 606/310
 See application file for complete search history.

(56) References Cited

U.S. PATENT DOCUMENTS

| | | | | |
|---|---|---|---|---|
| 6,558,388 | B1* | 5/2003 | Bartsch | A61B 17/7225 606/62 |
| 2005/0182405 | A1* | 8/2005 | Orbay | A61B 17/8047 606/289 |
| 2012/0130502 | A1 | 5/2012 | Podolsky et al. | |
| 2012/0197315 | A1* | 8/2012 | Kim | A61B 17/7032 606/305 |

FOREIGN PATENT DOCUMENTS

| | | |
|---|---|---|
| SE | 535 436 | 8/2012 |
| SE | 535 531 | 9/2012 |
| SE | 431 053 | 1/2016 |
| WO | 03/086214 | 10/2003 |
| WO | 2005072284 | 8/2005 |
| WO | 2008038286 | 4/2008 |

* cited by examiner

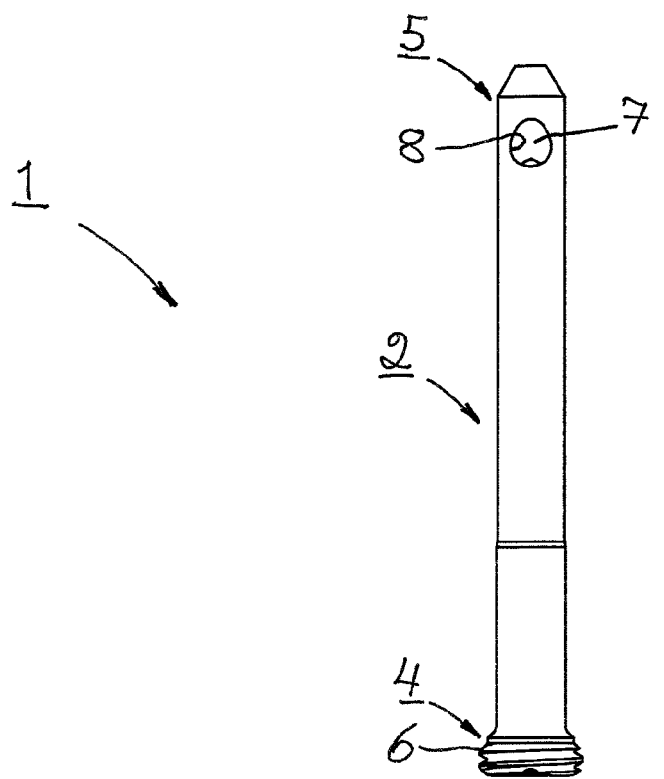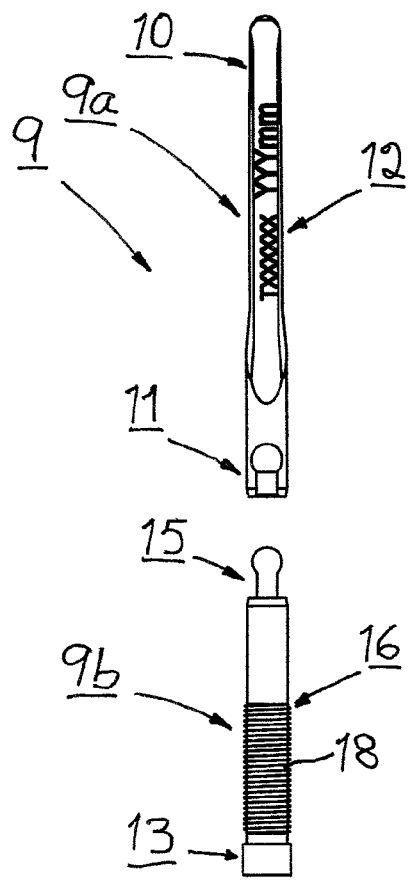
Fig. 1

A  B

A       B

A    B

A    B

A    B

FIXING MEANS FOR FIXATION OF BONE FRAGMENTS AT BONE FRACTURES

RELATED APPLICATIONS

This application corresponds to PCT/SE2012/061096, filed Oct. 12, 2012, the subject matter, of which is incorporated herein by reference in its entirety.

TECHNICAL FIELD

The present invention relates to a fixing means for fixation of bone fragments at bone fractures, wherein the fixing means comprises a sleeve and at least one pin which is provided in said sleeve, wherein the sleeve has an open rear end portion and a front end portion with at least one opening in a longitudinal side of the sleeve, wherein the pin is configured to be displaced in a forward direction relative to the sleeve for driving at least one front end portion of the pin out of the sleeve through said opening and into bone material in one of the bone fragments, wherein said front end portion of the pin, in operative position, extends out of the sleeve through the opening therein and engages the bone material in said one bone fragment, and wherein the pin is configured to be displaced in a backward direction relative to the sleeve for retracting the front end portion of the pin out of the bone material in said one bone fragment and into the sleeve.

BACKGROUND OF THE INVENTION

Driving devices and retraction devices for fixing means of the above type are known in several embodiments.

Driving devices are described in e.g. SE 431 053 B and SE 535 531 C2. The driving device of said first publication operates satisfactory, but has a relative complex construction and the handling thereof is circumstantial. The driving device of said latter publication also operates satisfactory and has also a less complex construction. It comprises a driving means which to a great extent is similar to a screw. The driving means, which is a separate member, is inserted into the open rear end portion of the sleeve, is brought to engage an internal thread in the sleeve and is further brought to engage a rear portion of the pin in the sleeve, and by continuously screwing the driving means into the sleeve, the pin is driven forward in a driving direction relative to the sleeve and the front end portion of the pin is driven out of through the opening in the sleeve and into the bone material in one of the bone fragments.

Retraction devices are defined in e.g. SE 433 166 B and SE 535 436 C2. The retraction device of said first publication operates satisfactory, but has, as the driving device of the above-mentioned SE 431 053 B, a relative complex construction and the handling thereof is circumstantial. The retraction device of said latter publication also operates satisfactory and has also a less complex construction. It comprises a retraction means which to a great extent is similar to a very short screw with an internal, but not an external threading. The retraction means, which is a separate member, is inserted into the open rear end portion of the sleeve and threaded onto the rear portion of the pin while it at the same time is brought to engage the open rear end portion of the sleeve, and by continuously screwing the retraction means into the sleeve, the pin is pulled or displaced backwards in a retraction direction relative to the sleeve and the retraction means, and the front end portion of the pin is retracted out of the bone material in the bone fragment in question and into the sleeve through the opening therein.

A drawback with these prior art driving and retraction devices is that they consist of separate, relatively small members which are easy to mislay and they can be used only for driving the pin of the fixing means and only for retraction of the pin of the fixing means respectively.

SUMMARY OF THE INVENTION

An object of the present invention is therefore, to instead configure the pin of the fixation means in a simple way such that said pin can be driven into and retracted out of the bone material in the bone fragment in question without the use of separate driving and retraction means which can be mislaid.

This is achieved according to the invention by means of a fixing means with the characterizing features of claim 1, i.e. by providing the pin of the fixing means to comprise a fixing member with the front end portion and a driving and retraction member which is rotatably connected to the fixing member, and by configuring the driving and retraction member of the pin to, during rotation in a first direction of the driving and retraction member relative to the fixing member of the pin, displace the pin in a forward direction relative to the sleeve for driving the front end portion of the pin out of the sleeve and into the bone material in said one bone fragment and, during rotation in a second, opposite direction of the driving and retraction member relative to the fixing member, displace the pin in a backward direction relative to the sleeve for retracting or pulling the front end portion of the pin out of the bone material in said one bone fragment and into the sleeve.

By this two-part arrangement of the pin of the fixing means, wherein one member of the pin is configured for use as a driving as well as retraction means, the need of special separate driving and retraction means for this driving and retraction respectively, of the fixing means into and out of the bone material in the bone fragment in question, is eliminated.

Preferred embodiments of the fixing means of the invention are defined in the dependent claims 2-33.

BRIEF DESCRIPTION OF THE DRAWINGS (OPTIONAL)

Figure 3:
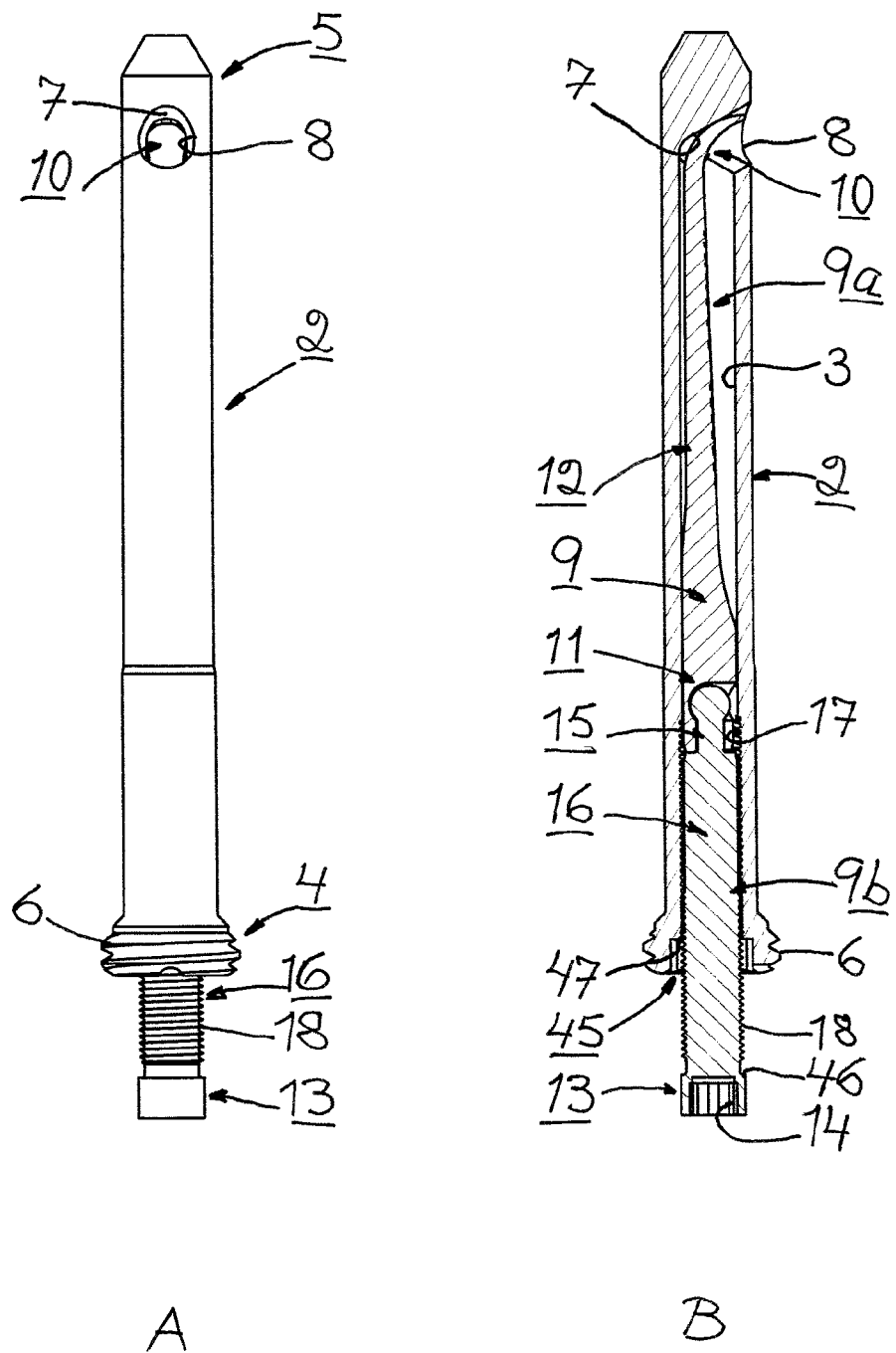
Figure 4:
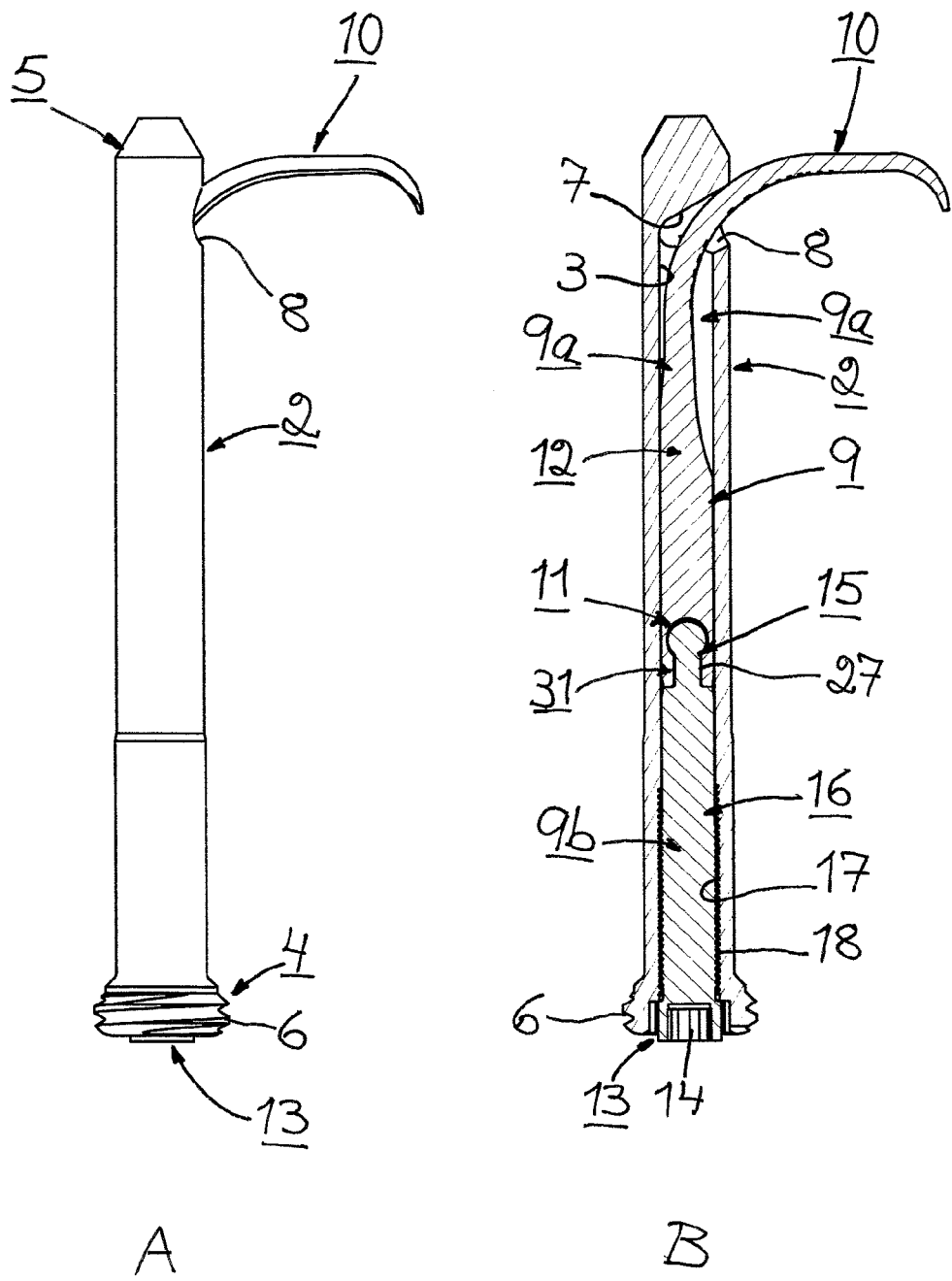
Figure 5:
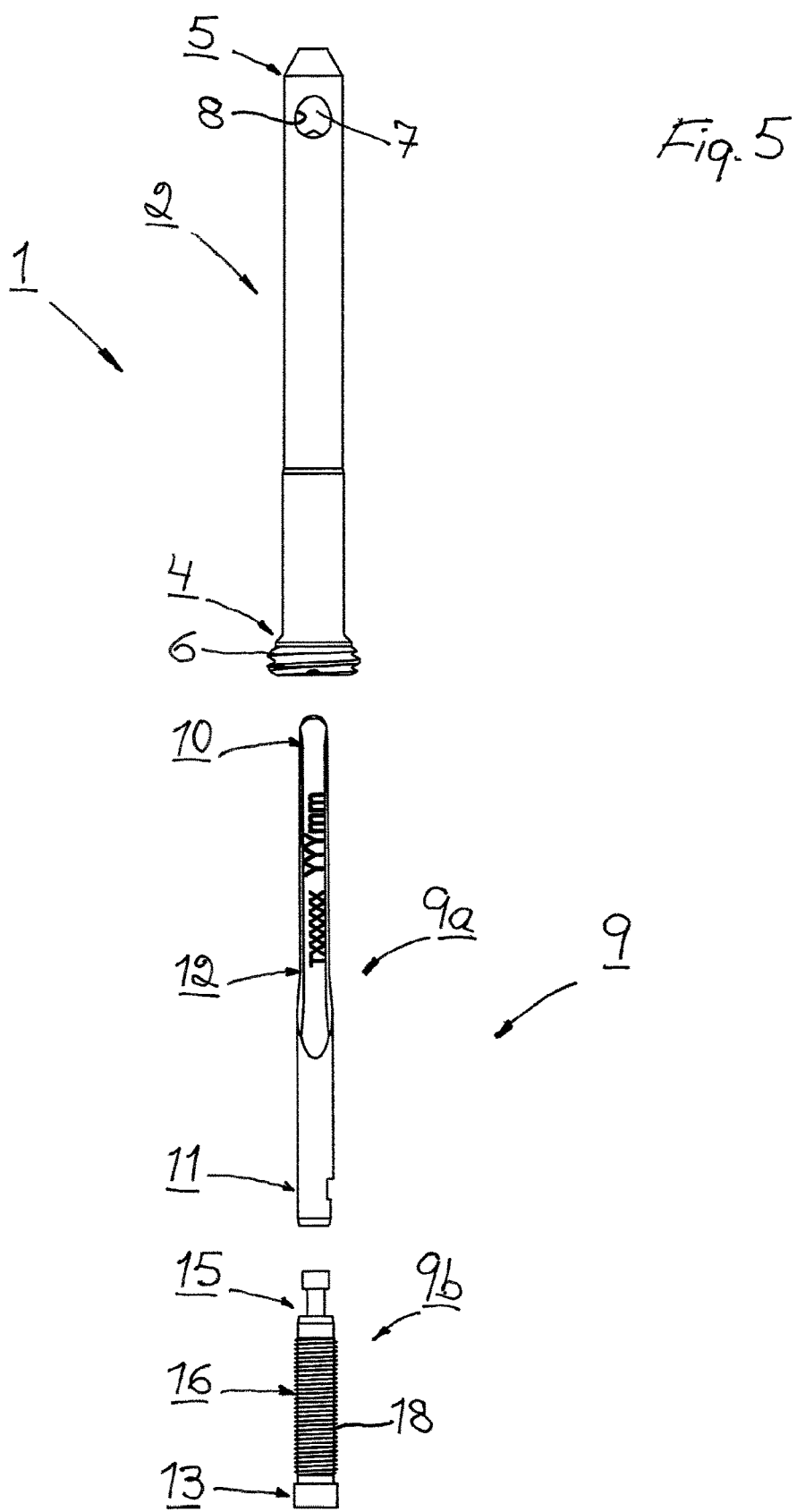
Figure 6:
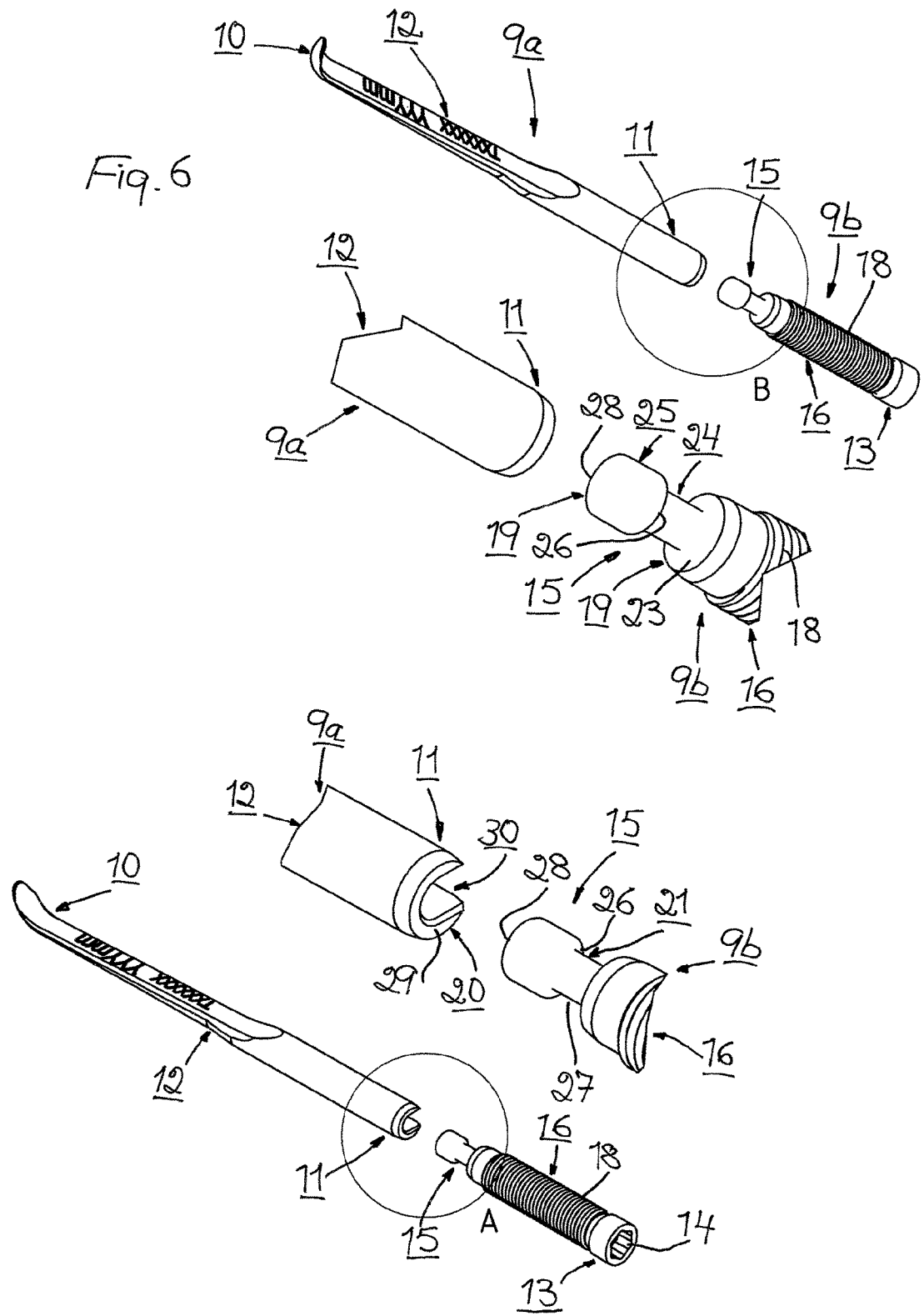
Figure 7:
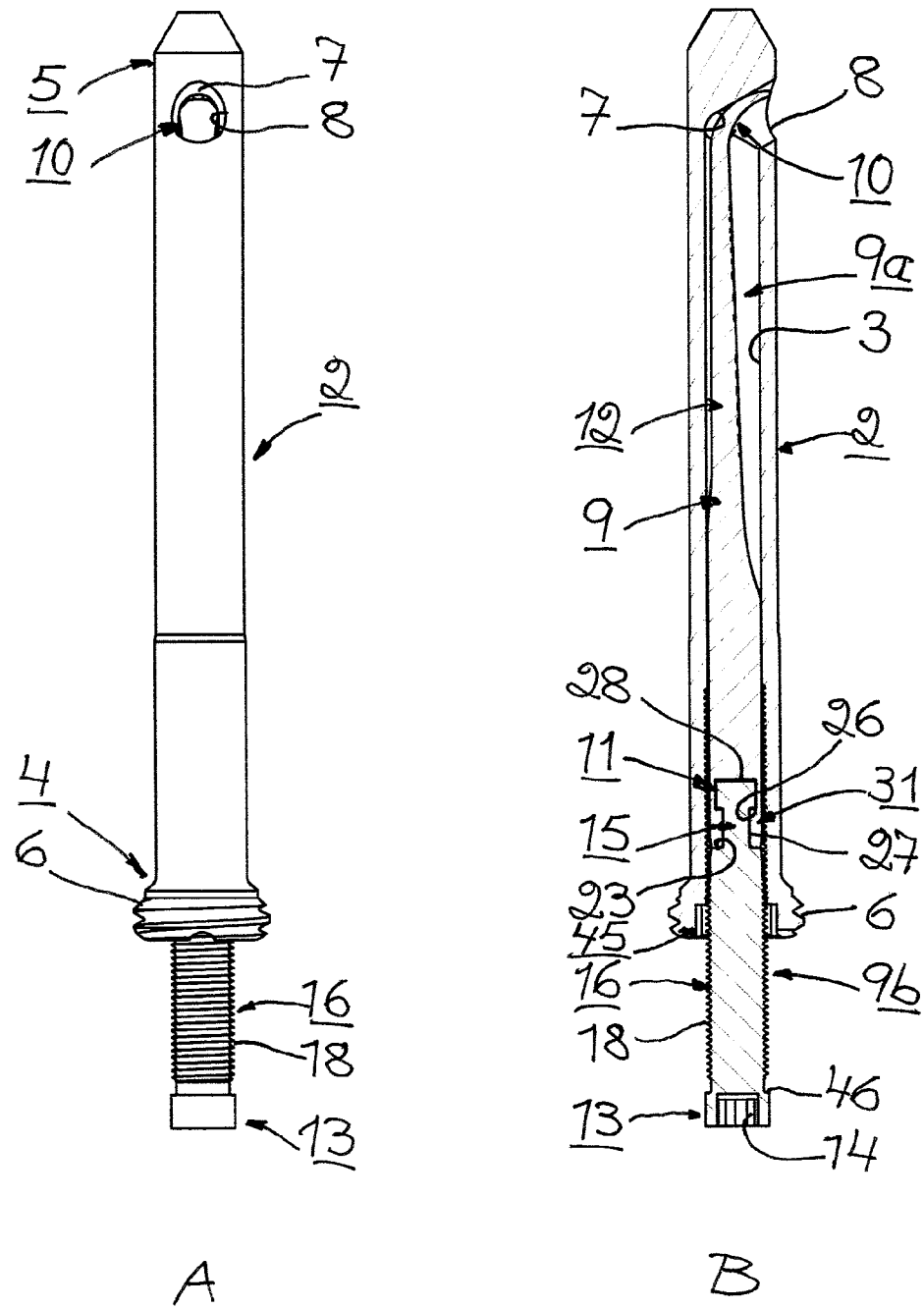
Figure 8:
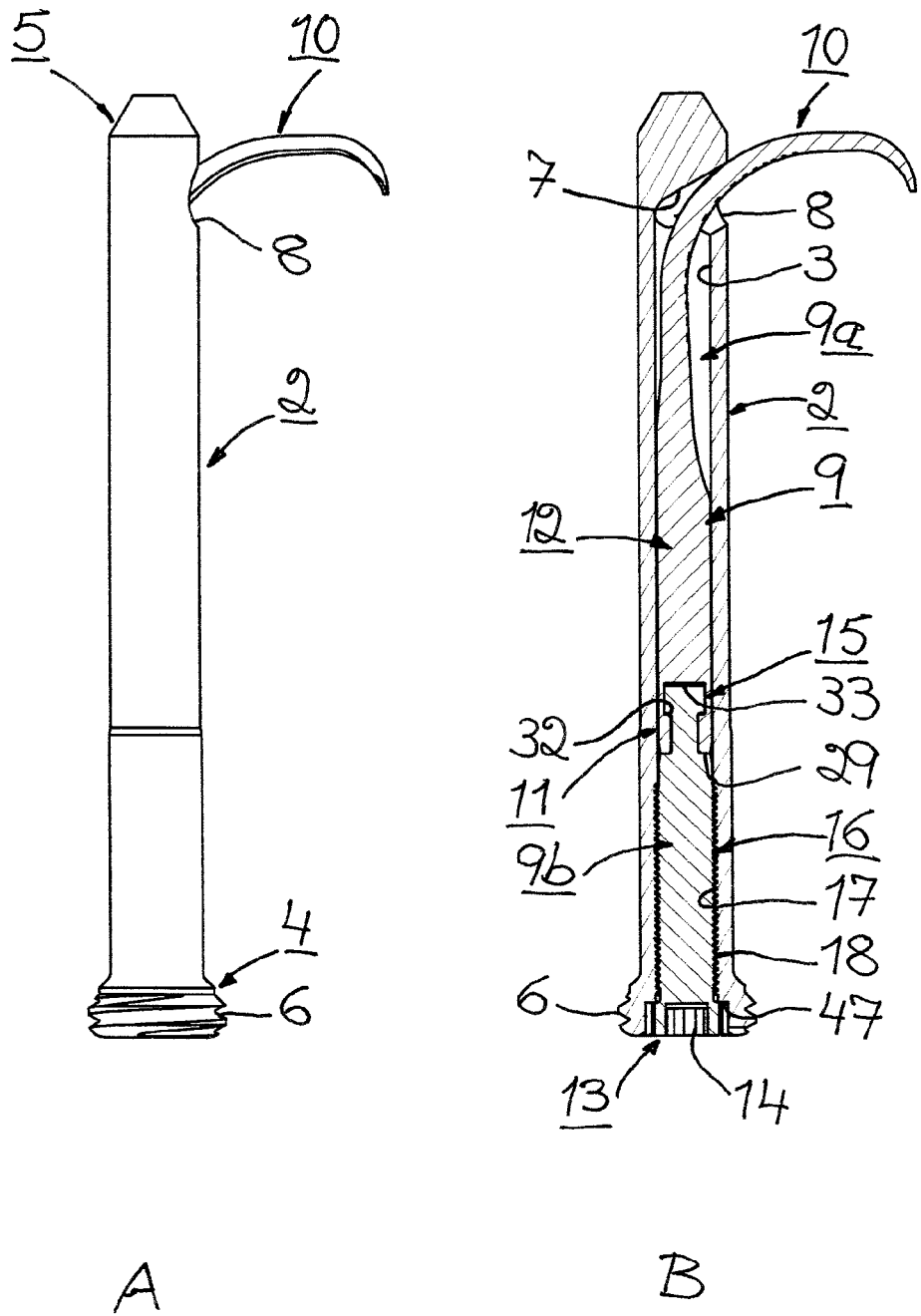
Figure 9:
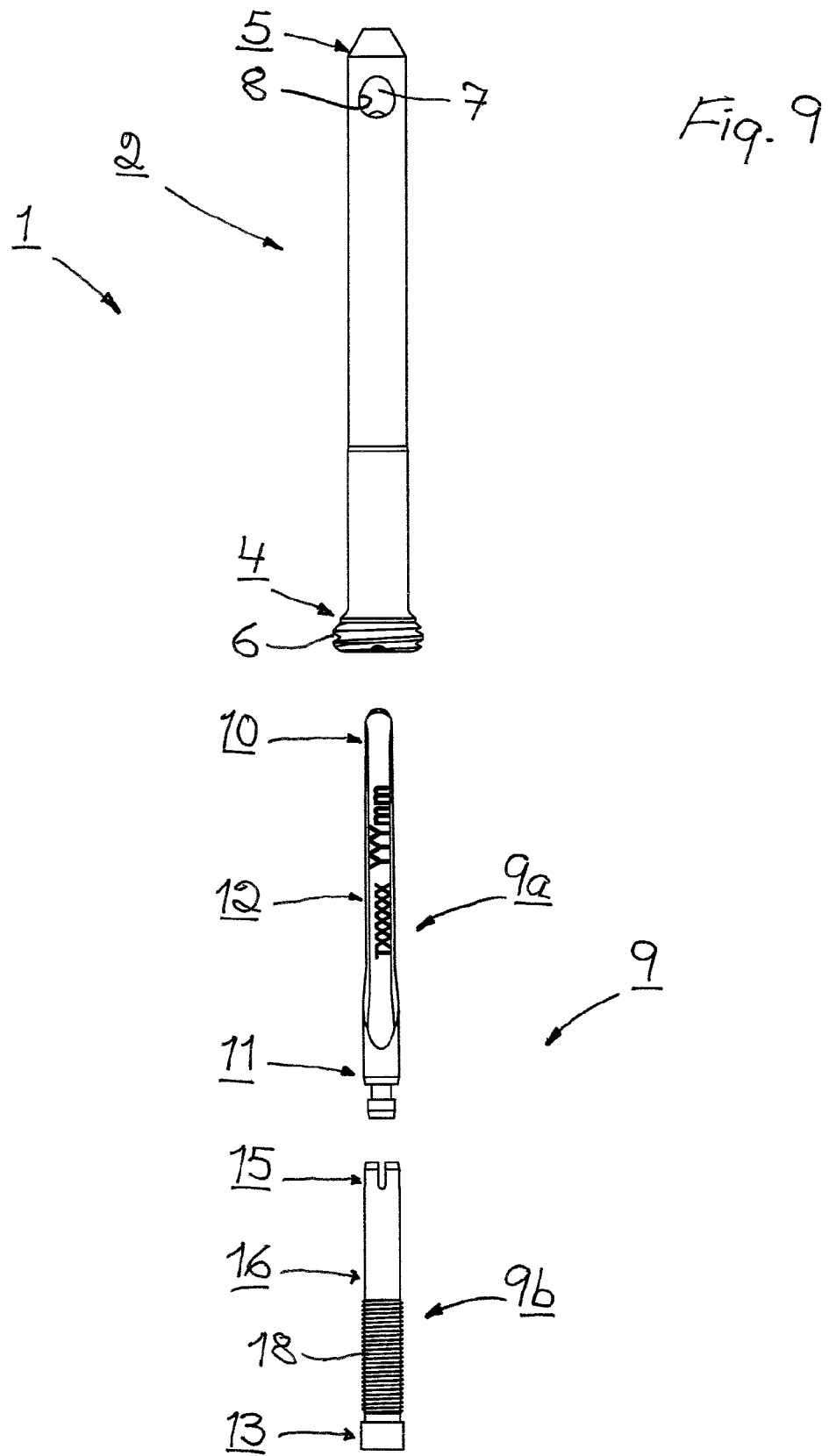
Figure 10:
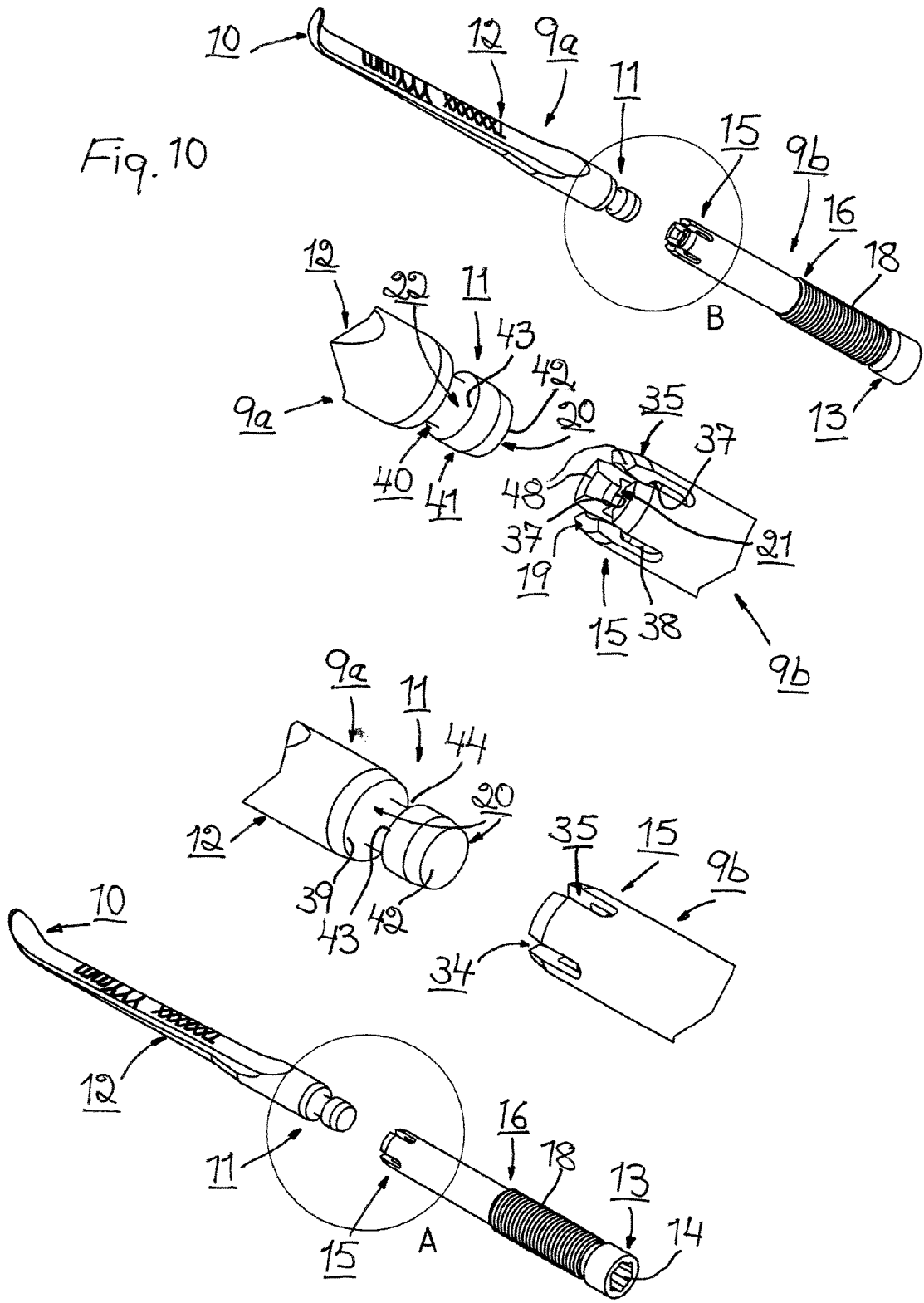
Figure 11:
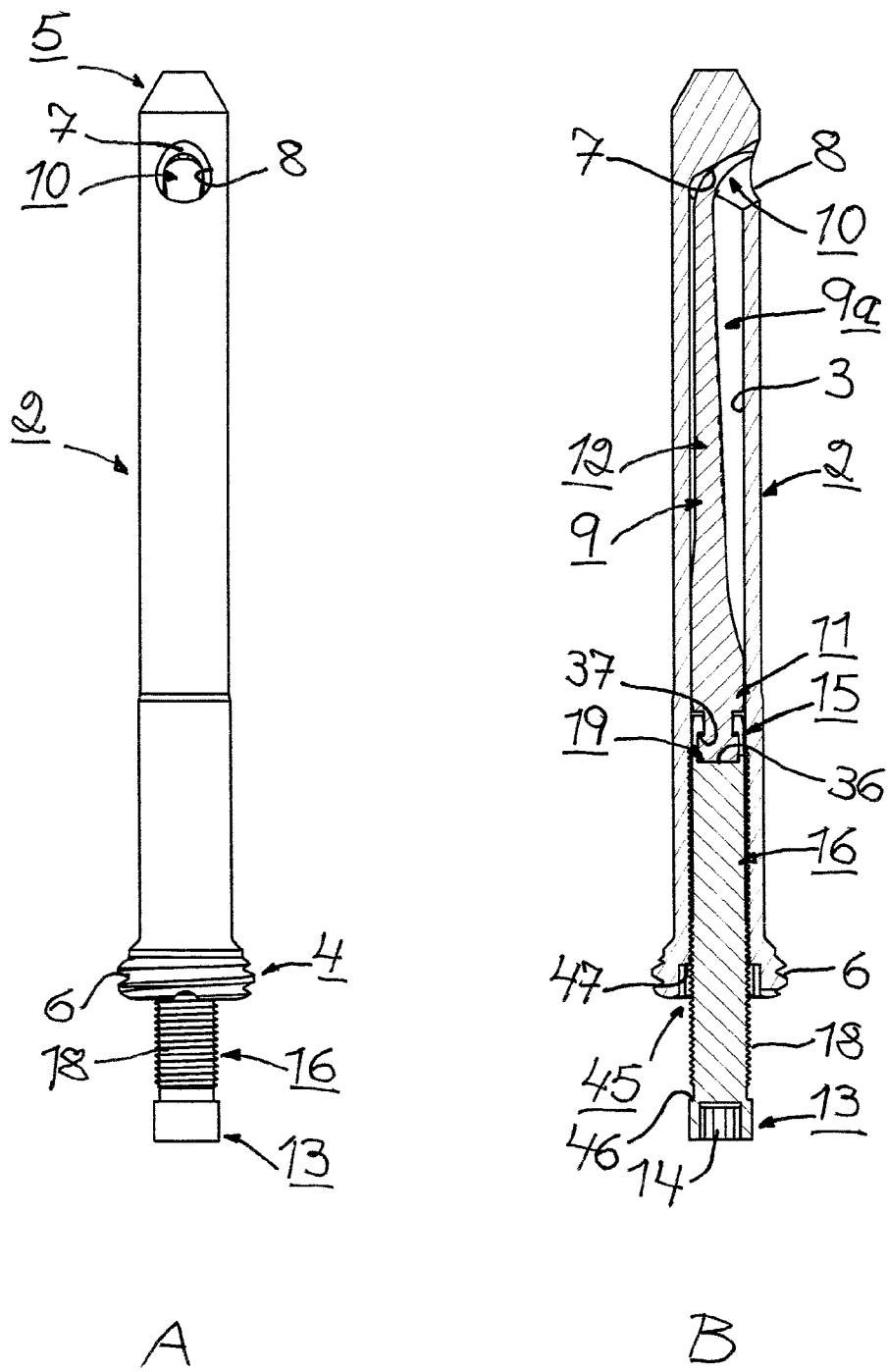
Figure 12:
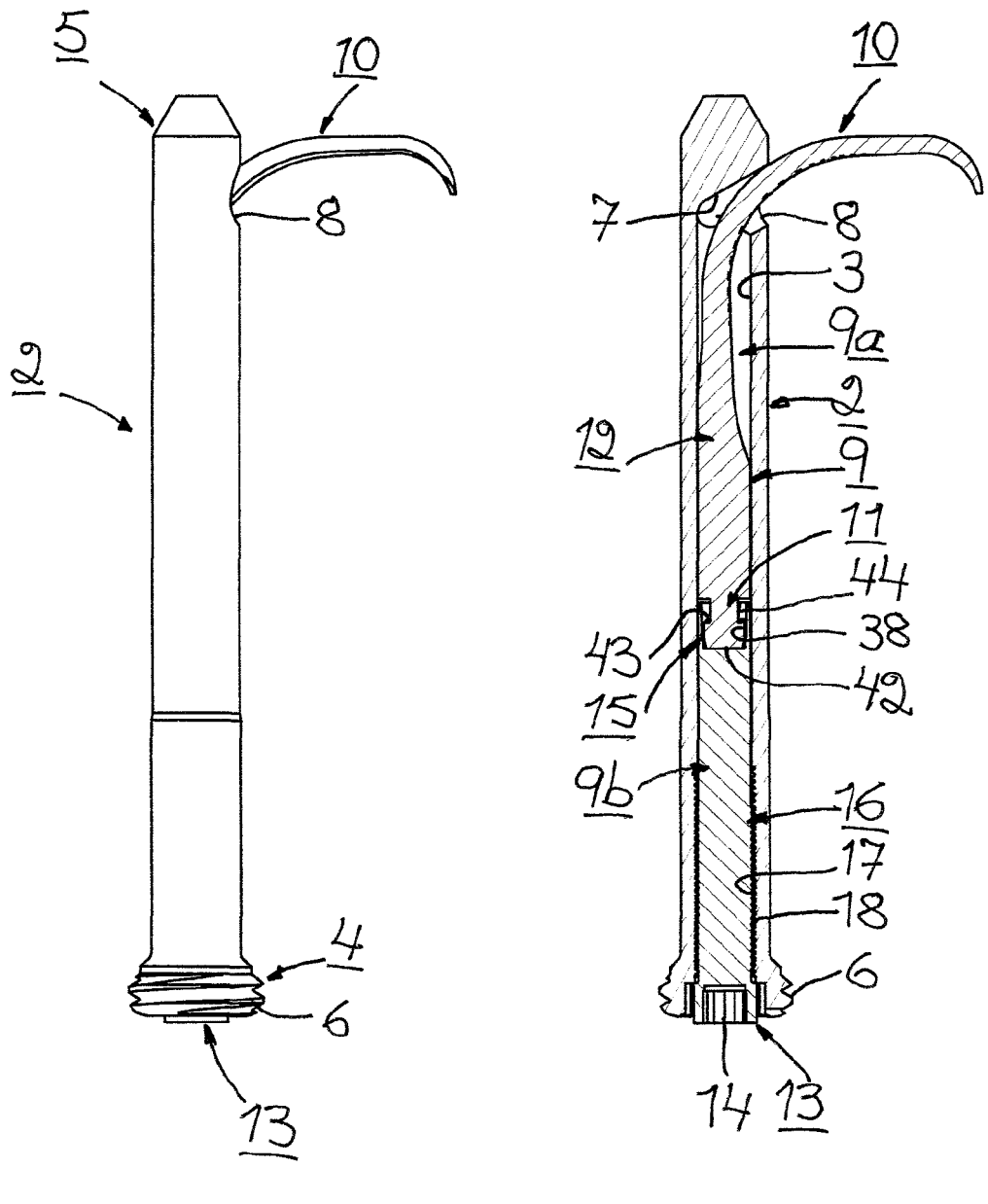

The invention will be further described below with reference to the accompanying drawings, in which FIG. 1 with an exploded side view illustrates a first embodiment of a fixing means according to the invention;

FIGS. 2A and 2B with perspective views and with parts thereof enlarged illustrate the pin of the fixing means of FIG. 1;

FIGS. 3A and 3B with a side view and a sectional view illustrate the fixing means of FIG. 1 in ready position;

FIGS. 4A and 4B with a side view and a sectional view illustrate the fixing means of FIG. 1 in operative position;

FIG. 5 with an exploded side view illustrates a second embodiment of a fixing means according to the invention;

FIGS. 6A and 6B with perspective views and with parts thereof enlarged illustrate the pin of the fixing means of FIG. 5;

FIGS. 7A and 7B with a side view and a sectional view illustrate the fixing means of FIG. 5 in ready position;

FIGS. 8A and 8B with a side view and a sectional view illustrate the fixing means of FIG. 5 in operative position;

FIG. 9 with an exploded side view illustrates a third embodiment of a fixing means according to the invention;

FIGS. 10A and 10B with perspective views and with parts thereof enlarged illustrate the pin of the fixing means of FIG. 9;

FIGS. 11A and 11B with a side view and a sectional view illustrate the fixing means of FIG. 9 in ready position; and FIGS. 12A and 12B with a side view and a sectional view illustrate the fixing means of FIG. 9 in operative position.

DETAILED DESCRIPTION OF PREFERRED EMBODIMENTS

A fixing means in various embodiments for fixation of bone fragments at bone fractures is illustrated in the accompanying drawing figures. The bone fragments to be fixed can be bone fragments at femoral fractures, collar bone fractures or fractures on any other bone in the body. The fixing means is to a great extent constructed as the fixing means according to the above-mentioned publications, which are referred to for further details of the function of the fixing means.

Thus, the fixing means 1 comprises a cylindrical sleeve 2 with a passage 3 which is open at the rear end portion 4 of the sleeve, but closed at the front end portion 5 of the sleeve. The rear end portion 4 of the sleeve 2 is configured with an external thread 6 for attachment by screwing of the fixing means 1 directly into a bone or to a securing plate (not shown) of an implant for positioning of several fixing means for fixation of bone fragments at a bone fracture, whereby the securing plate has threaded holes for the fixing means. Alternative ways to attach fixing means to the securing plate exist. The fixing means 1 may e.g. be clamped to the securing means by means of any type of clamping means or by means of a locking means with threads which is screwed into the threaded holes in the securing plate. The passage 3 in the sleeve 2 has at least one forward limiting surface 7 which is oblique and ends at at least one opening 8 in a longitudinal side of the sleeve 2.

The fixing means further comprises at least one pin 9 which is provided in the passage 3 in the sleeve 2 and which in the illustrated embodiment protrudes backwards from the rear end of the sleeve. The pin 9 is in the views according to FIGS. 3A and 3B, 7A and 7B and 11A and 11B respectively, illustrated as being in ready position in the sleeve 2. The pin 9 comprises at least one front end portion 10 which is movable or displaceable in a forward direction in the sleeve 2 and out of the sleeve via the oblique forward limiting surface 7 and the side opening 8 in the sleeve and into bone material in one of the bone fragments. This front end portion 10 of the pin 9 extends, when in operative position, out of the sleeve 2 through the opening 8 and engages the bone material in said one bone fragment. Hereby, the fixing means 1 fix the bone fragments to each other. The pin 9 is in the views according to FIGS. 4A and 4B, 8A and 8B and 12A and 12B respectively, illustrated as being in operative position. If the fixing means 1 is attached directly to a bone, it may be suitable during driving of the pin 9 into the bone material to hold-on by means of a suitable instrument to prevent the sleeve from rotating. If desired, the pin 9 may be configured with more than one front end portion 10.

According to the invention, the pin 9 comprises two members, namely a fixing member 9a with said front end portion 10 and a driving and retraction member 9b which is rotatably connected to the fixing member. The driving and retraction member 9b of the pin 9 is configured to, during rotation in a first direction of the driving and retraction member relative to the fixing member 9a of the pin, displace the pin in a forward direction relative to the sleeve 2 for driving the front end portion 10 of the pin out of the sleeve and into the bone material in said one bone fragment. During rotation in a second, opposite direction of the driving and retraction member 9b relative to the fixing member 9a, the driving and retraction member pulls or displaces the pin 9 in a backward direction relative to the sleeve 2 for retracting the front end portion 10 of the pin out of the bone material in said one bone fragment and into the sleeve. During rotation e.g. in clockwise direction of the driving and retraction member 9b relative to the fixing member 9a, the front end portion 10 of the pin 9 may be driven into the bone material in the bone fragment in question, and during rotation in counter-clockwise direction of the driving and retraction member relative to the fixing member, the front end portion of the pin can be pulled out of or retracted from the bone material. This means that the driving and retraction member 9b can be manoeuvred as a conventional screw. It is impossible to make mistakes and no separate driving and retraction members are needed, which are easily lost. Within the scope of the invention however, it is possible to rotate the driving and retraction member 9b in counter-clockwise direction for driving the front end portion 10 of the pin 9 into and rotate the driving and retraction member in clockwise direction for retracting or pulling the front end portion of the pin out of bone material respectively.

In the illustrated embodiments, the fixing member 9a of the pin 9 comprises, besides the front end portion 10 which at the front tapers to a point or tip, a coupling portion 11 at the rear of the fixing member and an intermediate portion 12 which connects the front end portion 10 to the coupling portion 11.

In the illustrated embodiments, the driving and retraction member 9b of the pin 9 comprises a rear end portion 13 with a seat 14 for a driving tool, a coupling portion 15 at the front of the driving and retraction member for rotatable connection to the coupling portion 11 at the rear of the fixing member 9a and an intermediate portion 16 which connects the end portion 13 with the seat for a driving tool to the coupling portion 15 of the driving and retraction member. The intermediate portion 16 is on the outside at least partly threaded for connection of the driving and retraction member 9b to the sleeve 2 of the fixing means 1 by inserting the driving and retraction member into the open rear end portion 4 of the sleeve and into engagement with an internal thread 17 in the sleeve. The intermediate portion 16 is preferably configured as a solid rod, but may alternatively be hollow. In the illustrated embodiments, the rear half of the intermediate portion 16 is provided with a thread 18 for engagement with the thread 17 inside the sleeve 2. This internal thread 17 is also provided in the rear part of the passage 3 in the sleeve 2, closest to the open rear end portion 4 of the sleeve. The threaded coupling results in that the pin 9 is always locked in the ready position according to FIGS. 3A and 3B, 7A and 7B and 11A and 11B respectively, and can not be pressed back.

The coupling portion 15 at the front of the driving and retraction member 9b of the pin 9 has at least one first engagement surface 19 which, for driving of the pin, is configured to be brought into engagement with at least one first engagement surface 20 on the coupling portion 11 at the rear of the fixing member 9a of the pin. By screwing the driving and retraction member 9b of the pin 9 into the sleeve 2 while the first engagement surface 19 on the coupling portion 15 of the driving and retraction member rotatably engages the first engagement surface 20 on the coupling portion 11 of the fixing member 9a, the driving and retraction member displaces the pin forward in a driving direction relative to the sleeve, such that the front end portion 10 of the pin is driven out through the side opening 8 in the sleeve and into the bone material in said one bone fragment. The attachment by screwing the driving and retraction member 9b into the sleeve 2 is performed by inserting a driving tool (not illustrated) of a suitable type, e.g. a screwdriver, into the complementary configured seat 14 in the rear end portion 13 of the driving and retraction member and rotating said tool in clockwise direction. The engagement of the threads 18, 17 on the outside of the intermediate portion 16 of the driving and retraction member 9b and in the passage 3 in the sleeve 2 respectively, drives the pin 9 in forward direction in the passage.

The coupling portion 15 at the front of the driving and retraction member 9b of the pin 9 also has at least one second engagement surface 21 which, for retraction of the pin, is configured to be brought into engagement with at least one second engagement surface 22 on the coupling portion 11 at the rear of the fixing member 9a of the pin. By screwing the driving and retraction member 9b out of the sleeve 2 while the second engagement surface 21 on the coupling portion 15 of the driving and retraction member rotatably engages the second engagement surface 22 on the coupling portion 11 of the fixing member 9a, the driving and retraction member displaces the pin backward in a retraction direction relative to the sleeve, such that the front end portion 10 of the pin is pulled out of the bone material in said one bone fragment and into the sleeve through the side opening 8 therein. The retraction by screwing out the driving and retraction member 9b in the sleeve 2 is performed by inserting a driving tool, e.g. the screwdriver for screwing in the driving and retraction member, into the complementary configured seat 14 in the rear end portion 13 of the driving and retraction member and rotating said tool in counter-clockwise direction. The engagement of the threads 18, 17 on the outside of the intermediate portion 16 of the driving and retraction member 9b and in the passage 3 in the sleeve 2 respectively, retracts or pulls the pin 9 in backward direction in the passage.

The seat 14 in the rear end portion 13 of the driving and retraction member 9b of the pin 9 may have any suitable shape for its intended use, e.g. consist of an internal hexagonal groove which is provided in said rear end portion for engagement in said groove of e.g. a correspondingly configured screwdriver. With this embodiment, it is prevented that soft tissue and/or bone tissue grows in over or onto the pin 9 and prevents retraction thereof.

As is apparent from the enclosed drawing figures, the pin 9 of the fixing means 1 according to the present invention may be configured in different ways, while the sleeve 2 of the fixing means is the same. Primarily, this means that particularly the coupling portions 11, 15 of the fixing and driving and retraction members 9a, 9b of the pin respectively, can be configured differently.

Thus, according to FIGS. 1 to 4 and FIGS. 5 to 8 respectively, the coupling portion 15 at the front of the driving and retraction member 9 b of the pin 9 is configured or defined by an end surface 23 on the intermediate portion 16 of the driving and retraction member 9 b and by a protruding member in the form of a tap 24, which protrudes substantially centrally from the end surface 23 and has a thicker part 25 on the free end of said tap. The end surface 23 on the intermediate portion 16, thus constituting a part of the coupling portion 15 of the driving and retraction member 9 b, has a first diameter, the tap 24 a second diameter which is smaller than the first diameter, and the thicker end part 25 on the tap a third diameter which is smaller than the first diameter but larger than the second diameter (see preferably FIG. 2B and FIG. 6B respectively). The end surface 23 on the intermediate portion 16 defines the first engagement surface 19 on the coupling portion 15 at the front of the driving and retraction member 9 b, and a surface 26 on the thicker end portion 25 of the tap 24 and substantially facing said first engagement surface defines the second engagement surface 21 on the coupling portion of the driving and retraction member. A groove or recess 27 for engaging the coupling portion 11, which is at the rear of the fixing member 9 a of the pin 9, is defined peripherally about the outside of the tap 24 between the first and second engagement surfaces 19, 21 on the coupling portion 15 at the front of the driving and retraction member 9 b. From FIGS. 1 to 4 it is apparent that the thicker end part 25 on the tap 24 is defined by a substantially spherical part, while it from FIGS. 5 to 8 is apparent that the thicker end part on the tap is formed by a substantially cylindrical or rod-like part. Other embodiments of the coupling portion 15 at the front of the driving and retraction member 9 b of the pin 9 are also possible. Thus, e.g. an end surface 28 on the thicker end part 25 of the tap 24 opposite to the surface 26 may serve as first engagement surface 19 on the coupling portion 15 of the driving and retraction member 9 b, either alone or, after precise dimensioning of the coupling portions 11, 15, together with the end surface 23 on the intermediate portion 16 of the driving and retraction member.

The coupling portion 11 at the rear of the fixing member 9a of the pin 9 has according to FIGS. 1 to 4 and FIGS. 5 to 8 respectively, an end surface 29 and a lateral groove or recess 30 in the coupling portion for insertion therein of the tap 24 and the thicker part 25 on the free end of the tap of the coupling portion 15 at the front of the driving and retraction member 9b of the pin. The lateral groove or recess 30 has a first width for insertion therein of the tap 24 and a second, in the illustrated embodiment greater width for insertion therein of the thicker part 25 on the free end of the tap. The shoulder 31 on the coupling portion 11 defined by said greater width engages the groove or recess 27 between the first and second engagement surfaces 19, 21 on the coupling portion 15 of the driving and retraction member 9b. The end surface 29 on the coupling portion 11 at the rear of the fixing member 9a of the pin 9 defines the first engagement surface 20 on said coupling portion, and a surface 32, facing substantially away from said first engagement surface and defining the second width of the groove or recess 30, i.e. a surface on the shoulder 31, defines the second engagement surface 22 on said coupling portion. From particularly FIGS. 2A and 2B it is apparent that where the lateral groove or recess 30 has a greater width for being able to receive the thicker part 25 on the free end of the tap 24, the groove or recess is correspondingly configured as a substantially spherical space, while it from FIGS. 6A and 6B is apparent that where the lateral groove or recess has a greater width, the groove or recess is configured as a substantially cylindrical space. Other embodiments of the coupling portion 11 at the rear of the fixing member 9a of the pin 9 are also possible. An end surface 33 in the groove or recess 30 may e.g. define the first engagement surface 20 on the coupling portion 11 of the fixing member 9a either alone or, after precise dimensioning of the coupling portions 11, 15 and then particularly the length of the tap 24 and the thicker part 25 on the tap and the length of the groove or recess 30 respectively, together with the end surface 29 on the coupling portion 11, and thereby cooperate with the end surface 28 on the thicker end part 25 of the tap 24.

When the pin 9 is screwed into the sleeve 2 and further forward in the driving direction, the first engagement surface 19 (end surface 23 and/or end surface 28) on the coupling portion 15 of the driving and retraction member 9b will consequently be pressed against the first engagement surface 20 (end surface 29 and/or end surface 33) on the coupling portion 11 of the fixing member 9a while said first engagement surface on the coupling portion of the driving and retraction member at the same time rotates relative to said first engagement surface on the coupling portion of the fixing member. When the pin 9 is screwed out in the retracting direction, the first engagement surface 19 on the coupling portion 15 of the driving and retraction member 9b will cease its engagement with the first engagement surface 20 on the coupling portion 11 of the fixing member 9a and instead, the second engagement surface 21 (surface 26) on the coupling portion 15 of the driving and retraction member is pressed against the second engagement surface 22 (surface 32) on the coupling portion 11 of the fixing member while said second engagement surface on the coupling portion of the driving and retraction member at the same time rotates relative to said second engagement surface on the coupling portion of the fixing member.

Since the groove or recess 27 peripherally outside of the tap 24, between the first and second engagement surfaces 19, 21 on the coupling portion 15, for the shoulder 31, which is defined between the first and second engagement surfaces 20, 22 on the coupling portion 11, in the illustrated embodiments is somewhat longer than the shoulder, the shoulder can easily engage or grip into said groove or recess. The groove or recess 30 for the tap 24 and the thicker end part 25 on the tap is of course also somewhat larger, i.e. has a somewhat greater width or diameter than said tap and said thicker end part in order to facilitate insertion of the coupling portion 15 of the driving and retraction member 9b into said groove or recess.

The configuration of the coupling portions 11, 15 of the various members 9a, 9b of the pin 9 may within the scope of the present invention also be the opposite, such that the coupling portion 11 is provided on the driving and retraction member 9b and the coupling portion 15 on the fixing member 9a.

According to FIGS. 9 to 12, the coupling portion 11 at the rear of the fixing member 9 a of the pin 9 is defined by a an end surface 39 on the intermediate portion 12 of the fixing member 9 a and by a protruding member in the form of a tap 40, which protrudes substantially centrally from the end surface 39 and has a thicker part 41 on the free end of said tap. The end surface 39 on the intermediate portion 12 of the fixing member 9 a has thereby a first diameter, the tap 40 a second diameter which is smaller than the first diameter and the thicker part 41 a third diameter which is smaller than the first diameter but larger than the second diameter. An end surface 42 on the thicker end part 41 on the tap 40 defines the first engagement surface 20 on the coupling portion 11 at the rear of the fixing member 9 a of the pin 9, and a surface 43 on the thicker end part on the tap, facing the end surface 39 but facing substantially away from said first engagement surface, defines the second engagement surface 22 on the coupling portion of the fixing member. A groove or recess 44 is defined peripherally about the outside of the tap 40 between the end surface 39 on the intermediate portion 12 of the fixing member 9 a and the second engagement surface 22 on the thicker end part 41 of the tap for insertion of the hook portion 35 at the front of the coupling portion 15 of the driving and retraction member 9 b of the pin 9 into said groove or recess. The configuration of the hook portion 35 and the thicker end part 41 of the tap 40 illustrated in FIGS. 9 to 12, will result in that the hook portion, when connecting the fixing member 9 a and the driving and retraction member 9 b, first expands outwards when it slides along said end part and then moves back by a snap-in action when the hook portion engages the groove or recess 44. Other configurations of the coupling portion 11 at the rear of the fixing member 9 a of the pin 9 are possible. The end surface 39 from which the tap 40 and the thicker end part 41 of the tap protrude, may e.g. define the first engagement surface 20 on the coupling portion 11 of the fixing member 9 a either alone or, after precise dimensioning of the coupling portions 11, 15 and then particularly the length of the tap and the thicker end part thereon and the length of the recess 34 respectively, together with the end surface 42 on said thicker end part, and thereby cooperate with the front end surface or surfaces 48 on the hook portion/hook portions 35.

According to FIGS. 9 to 12, the coupling portion 11 at the rear of the fixing member 9a of the pin 9 is defined by a substantially centrally from an end surface 39 on the intermediate portion 12 of the fixing member protruding member in the form of a tap 40 with a thicker part 41 on the free end of said tap. The end surface 39 on the intermediate portion 12 of the fixing member 9a has thereby a first diameter, the tap 40 a second diameter which is smaller than the first diameter and the thicker part 41 a third diameter which is smaller than the first diameter but larger than the second diameter. An end surface 42 on the thicker end part 41 on the tap 40 defines the first engagement surface 20 on the coupling portion 11 at the rear of the fixing member 9a of the pin 9, and a surface 43 on the thicker end part on the tap, facing the end surface 39 but facing substantially away from said first engagement surface, defines the second engagement surface 22 on the coupling portion of the fixing member. A groove or recess 44 is defined peripherally outside of the tap 40 between the end surface 39 on the intermediate portion 12 of the fixing member 9a and the second engagement surface 22 on the thicker end part 41 of the tap for insertion of the hook portion 35 at the front of the coupling portion 15 of the driving and retraction member 9b of the pin 9 into said groove or recess. The configuration of the hook portion 35 and the thicker end part 41 of the tap 40 illustrated in FIGS. 9 to 12, will result in that the hook portion, when connecting the fixing member 9a and the driving and retraction member 9b, first expands outwards when it slides along said end part and then moves back by a snap-in action when the hook portion engages the groove or recess 44. Other configurations of the coupling portion 11 at the rear of the fixing member 9a of the pin 9 are possible. The end surface 39 from which the tap 40 and the thicker end part 41 of the tap protrude, may e.g. define the first engagement surface 20 on the coupling portion 11 of the fixing member 9a either alone or, after precise dimensioning of the coupling portions 11, 15 and then particularly the length of the tap and the thicker end part thereon and the length of the recess 34 respectively, together with the end surface 42 on said thicker end part, and thereby cooperate with the front end surface or surfaces 48 on the hook portion/hook portions 35.

When the pin 9 is screwed into the sleeve 2 and further forward in the driving direction, the first engagement surface 19 (bottom 36 and/or end surface 48) on the coupling portion 15 of the driving and retraction member 9b is pressed against the first engagement surface 20 (end surface 42 and/or end surface 39) on the coupling portion 11 of the fixing member 9a while said first engagement surface on the coupling portion of the driving and retraction member at the same time rotates relative to said first engagement surface on the coupling portion of the fixing member. When the pin 9 is screwed out in the retracting direction, the first engagement surface 19 on the coupling portion 15 of the driving and retraction member 9b ceases its engagement with the first engagement surface 20 on the coupling portion 11 of the fixing member 9a and instead, the second engagement surface 21 (surface 37) on the coupling portion 15 of the driving and retraction member is pressed against the second engagement surface 22 (surface 43) on the coupling portion 11 of the fixing member while said second engagement surface on the coupling portion of the driving and retraction member at the same time rotates relative to said second engagement surface on the coupling portion of the fixing member.

The configuration according to FIGS. 9 to 12 of the coupling portions 11, 15 of the various members 9a, 9b of the pin 9 may within the scope of the present invention also be the opposite, such that the coupling portion 11 is provided on the driving and retraction member 9b and the coupling portion 15 on the fixing member 9a.

From the above it is obvious that the fixing member 9a and driving and retraction member 9b of the pin 9 are put together by connecting the coupling portions 11 and 15 respectively, of said members to each other and that this is done before the pin is placed in the sleeve 2. The coupling portions 11, 15 are connected to each other by, at the embodiments of FIGS. 1 to 4 and FIGS. 5 to 8 respectively, inserting the tap 24 and the thicker end part 25 of the tap into the groove or recess 30, and at the embodiment of FIGS. 9 to 12 by inserting the thicker end part 41 of the tap 40 into the recess 34 until the hook portion 35 snaps into or engages the groove or recess 44.

After the above-mentioned connection, the pin 9 is inserted into the sleeve 2 until engagement with the thread 17 inside the sleeve is obtained by means of the thread 18 on the outside of the driving and retraction member 9b of the pin, whereupon the pin is brought to the ready position by rotating/screwing in the driving and retraction member thereof such that the pin is screwed further into the sleeve. By this arrangement of the pin 9 in the sleeve 2, the first engagement surface 19 on the coupling portion 15 of the driving and retraction member 9b is rotatably engaging the first engagement surface 20 on the coupling portion 11 of the fixing member 9a of the pin and displaces said fixing member in forward direction towards the ready position. By means of the engagement of the threads 17, 18 and with the front end portion 10 of fixing member 9a of the pin 9 in the ready position according to FIGS. 3A and 3B, 7A and 7B and 11A and 11B respectively, adjacent to or even in engagement with the oblique forward limiting surface 7 and with the tip of the front end portion situated close to or in the side opening 8 in the sleeve 2, the pin is locked in a position such that said pin can neither rotate nor turn the wrong way, be pushed forward in axial direction or in any other way be imparted an undesired movement during subsequent handling of the fixing means 1 such as transport and preparation for surgery.

When the pin 9 after connection of the fixing member 9a and driving and retraction member 9b thereof and after having been inserted into the sleeve 2 such that the front end portion 10 of the fixing member of the pin as mentioned is located in ready position close to the oblique forward limiting surface 7 and the opening 8 in the sleeve according to FIGS. 3A and 3B, 7A and 7B and 11A and 11B respectively, the fixing means 1 is ready for use.

By rotating the driving and retraction member 9b relative to the fixing member 9a in a first direction as defined above, the pin 9 can be displaced in a forward driving direction relative to the sleeve 2. This can go on until the end portion 13 with the seat 14 for a driving tool on the driving and retraction member 9b of the pin 9 engages the open rear end portion 4 of the sleeve 2, whereby preferably the driving and retraction member and the sleeve are configured such that, when this occurs, the front end portion 10 of the fixing member 9a of the pin is driven out as far as possible through the side opening 8 in the sleeve. Said end portion 13 has preferably a stop surface for engagement with an end surface on the open rear end portion 4 of the sleeve 2. Said end portion 13 may thereby preferably also be configured for locking the fixing means 1 to a securing plate, e.g. instead of the open rear end portion 4 of the sleeve 2 be threaded for cooperation with a thread on the securing plate for attaching by screwing of the fixing means to the securing plate behind said rear end portion 4 of the sleeve. As an alternative, as shown in the illustrated embodiments, the pin 9 may be displaced in forward driving direction relative to the sleeve 2 until the end portion 13 with the seat 14 for a driving tool of the driving and retraction member 9b of the pin engages a seat 45 for a driving tool in the open rear end portion 4 of the sleeve. Again, the driving and retraction member 9b of the pin 9 and the sleeve 2 are preferably configured such that when the end portion 13 with the seat 14 for a driving tool of the driving and retraction member engages the seat 45 for a driving tool in the open rear end portion 4 of the sleeve, the front end portion 10 of the fixing member 9a of the pin is driven out as far as possible through the side opening 8 in the sleeve. At this alternative embodiment, the end portion 13 with the seat 14 for a driving tool of the driving and retraction member 9b of the pin 9 preferably also has a stop surface 46 for engagement with a bottom surface 47 of the seat 45 for a driving tool in the open rear end portion 4 of the sleeve 2.

During displacement in the driving direction of the front end portion 10 of the fixing member 9a of the pin 9, the first engagement surface 19 on the coupling portion 15 of the driving and retraction member 9b maintains its rotatable engagement with the first engagement surface 20 on the fixing member 9a of the pin.

Retraction of the front end portion 10 of the fixing member 9a of the pin 9 is achieved by rotating the driving and retraction member 9b of the pin in an opposite direction as during the displacement of said front end portion in the driving direction. Thereby, the engagement with each other of the first engagement surfaces 19, 20 on the coupling portions of said members ceases and instead, the second engagement surface 21 on the coupling portion 15 of the driving and retraction member 9b is brought to engage the second engagement surface 22 on the coupling portion 11 of the fixing member 9a.

It is obvious to a skilled person that the fixing means 1 according to the present invention is not limited to the embodiments described above and illustrated in the drawings, but may vary within the scope of the subsequent claims without departing from the idea and purpose of the invention. The fixing means 1 may e.g. consist of a metal, e.g. a titanium alloy or steel, but may as an alternative consist of another for the purpose suitable material or of combinations of various suitable materials. The fixing means 1 and its various members may also have any for the purpose suitable shape, size and configuration other than those illustrated in the drawings. Regarding the size, the various members of the fixing means 1, i.e. the sleeve 2, the fixing member 9*a* of the pin 9 and the driving and retraction member 9*b* of the pin may vary, such that the length of the sleeve and of the fixing member of the pin is the same, while the length of the driving and retraction member of the pin varies with the length of the implant. Shape, size and configuration also of the various portions 10, 11 and 12 and 13, 15 and 16 respectively, of the fixing member 9*a* and driving and retraction member 9*b* of the pin 9 may vary beyond what is described above. The seat 14 for a driving tool in the rear end portion 13 of the driving and retraction member 9*b* of the pin 9 for screwing the pin into the sleeve 2 and displace the pin in a forward driving direction, may consist of e.g. a conventional hexagonal groove for a complementary screwdriver. The seat 14 may also have any other shape permitting adequate, safe insertion therein of a suitable driving tool. As an alternative, it is possible to configure the fixing means 1 with more than one pin 9 and/or, as indicated above, configure the pin or each pin of the fixing means with more than one front end portion 10 for engagement with the bone material and the sleeve of the fixing means with more than one side opening 8 for these front end portions. This can be achieved in a simple way by e.g. configuring the fixing member 9*a* of the pin 9 such that the intermediate portion 12 of the fixing member is branching-off and transforms into the required number of front end portions 10, e.g. two or four front end portions located with an angular displacement of 180° and 90° respectively, relative to each other, and configure the sleeve 2 with a corresponding number of side openings 8 located correspondingly on the sleeve. The intermediate portion 12 of the fixing member 9*a* may, as an alternative, be provided with the desired number of front end portions 10 without prior branching-off of the intermediate portion.

The invention claimed is:

1. A fixing means (1) for fixation of bone fragments at bone fractures, wherein the fixing means (1) comprises a sleeve (2) and at least one pin (9), which is provided in said sleeve,
   wherein the sleeve (2) has an open rear end portion (4) and a front end portion (5) with at least one opening (8) in a longitudinal side of the sleeve, wherein the at least one pin (9) is configured to be displaced in a forward direction relative to the sleeve (2) for driving at least one front end portion (10) of the at least one pin (9) out of the sleeve through the at least one opening (8) therein and into bone material in one of the bone fragments,
   wherein the at least one front end portion (10) of the at least one pin (9), in an operative position, extends out of the sleeve (2) through the at least one opening (8) therein and is configured to engage the bone material in said one bone fragment,
   wherein the at least one pin (9) is configured to be displaced in a backward direction relative to the sleeve (2) for retracting the at least one front end portion (10) of the at least one pin (9) out of the bone material in said one bone fragment and into the sleeve (2), and
   wherein the at least one pin (9) comprises a fixing member (9*a*), which is formed in one piece with the at least one front end portion (10), and a driving and retraction member (9*b*), which is rotatably connected to the fixing member (9*a*), and that the driving and retraction member (9*b*) of the at least one pin (9) is configured to, during rotation in a first direction of the driving and retraction member (9*b*) relative to the fixing member (9*a*) of the at least one pin (9), displace the fixing member (9*a*) and the driving and retraction member (9*b*) of the at least one pin (9) in a forward direction relative to the sleeve (2) for driving the at least one front end portion (10) of the at least one pin (9) out of the sleeve (2) and into the bone material in said one bone fragment and, during rotation in a second, opposite direction of the driving and retraction member (9*b*) relative to the fixing member (9*a*), displace the fixing member (9*a*) and the driving and retraction member (9*b*) of the at least one pin (9) in a backward direction relative to the sleeve (2) for retracting or pulling the at least one front end portion (10) of the at least one pin (9) out of the bone material in said one bone fragment and into the sleeve (2).

2. The fixing means according to claim 1, wherein the fixing member (9*a*) of the at least one pin (9) comprises, besides the at least one front end portion (10), a coupling portion (11) at the rear of the fixing member (9*a*) and an intermediate portion (12) which connects the at least one front end portion (10) to the coupling portion (11), and that the driving and retraction member (9*b*) of the at least one pin (9) comprises a rear end portion (13) with a seat (14) for a driving tool, a coupling portion (15) at the front of the driving and retraction member (9*b*) for rotatable connection to the coupling portion (11) at the rear of the fixing member (9*a*) and an intermediate portion (16) which connects the rear end portion (13) with the seat (14) for a driving tool to the coupling portion (15) of the driving and retraction member (9*b*) and which on the outside is at least partly threaded for connection of the driving and retraction member (9*b*) to the sleeve (2) of the fixing means (1) by inserting the driving and retraction member (9*b*) into the open rear end portion (4) of the sleeve (2) and into engagement with an internal thread (17) in the sleeve (2).

3. The fixing means according to claim 2, wherein the coupling portion (15) at the front of the driving and retraction member (9*b*) of the at least one pin (9) has at least one first engagement surface (19) which, for driving of the at least one pin (9), is configured to be brought into engagement with at least one first engagement surface (20) on the coupling portion (11) at the rear of the fixing member (9*a*) of the at least one pin (9), whereby, by screwing the driving and retraction member (9*b*) of the at least one pin (9) into the sleeve (2) while the at least one first engagement surface (19) on the coupling portion (15) of the driving and retraction member (9*b*) rotatably engages the at least one first engagement surface (20) on the coupling portion (11) of the fixing member (9*a*), the driving and retraction member (9*b*) displaces the at least one pin (9) forward in a driving direction relative to the sleeve (9), such that the at least one front end portion (10) of the at least one pin (9) is driven out through the at least one opening (8) in the sleeve (2) and into the bone material in said one bone fragment, and that the coupling portion (15) of the driving and retraction member (9*b*) has at least one second engagement surface (21) which, for retraction of the at least one pin (9), is configured to be brought into engagement with at least one second engagement surface (22) on the coupling portion (11) of the fixing member (9*a*), whereby, by screwing the driving and retraction member (9*b*) out of the sleeve (2) while the at least one second engagement surface (21) on the coupling portion (15) of the driving and retraction member (9*b*) rotatably engages the at least one second engagement surface (22) on the coupling portion (11) of the fixing member (9*a*), the driving and retraction member (9*b*) displaces the at least one pin (9) backward in a retraction direction relative to the sleeve (2), such that the at least one front end portion (10) of the at least one pin (9) is pulled out of the bone material in said one bone fragment and into the sleeve (2) through the at least one opening (8) therein.

4. The fixing means according to claim 3, wherein the coupling portion (15) at the front of the driving and retraction member (9b) of the at least one pin (9) is configured or defined by an end surface (23) on the intermediate portion (16) of the driving and retraction member (9b) and by a protruding member in the form of a tap (24), which protrudes substantially centrally from the end surface (23) and has a thicker part (25) on the free end of the tap (24).

5. The fixing means according to claim 4, wherein the end surface (23) on the intermediate portion (16) of the driving and retraction member (9b) of the at least one pin (9) has a first diameter, the tap (24) a second diameter which is smaller than the first diameter, and the thicker end part (25) on the tap (24) a third diameter which is smaller than the first diameter but larger than the second diameter.

6. The fixing means according to claim 4, wherein the end surface (23) on the intermediate portion (16) defines the at least one first engagement surface (19) on the coupling portion (15) at the front of the driving and reaction member (9b), and that a surface (26) on the thicker end portion (25) of the tap (24), substantially facing the at least one first engagement surface (19), defines the at least one second engagement surface (21) on the coupling portion (15) of the driving and retraction member (9b).

7. The fixing means according to claim 6, wherein a groove or recess (27) for engaging the coupling portion (11), which is at the rear of the fixing member (9a) of the at least one pin (9), is defined peripherally about the outside of the tap (24) between the at least one first and at least one second engagement surfaces (19, 21) on the coupling portion (15) at the front of the driving and retraction member (9b).

8. The fixing means according to claim 4, wherein an end surface (28) on the thicker end part (25) of the tap (24) serves as the at least one first engagement surface (19) on the coupling portion (15) of the driving and retraction member (9b), and that a surface (26) on the thicker end portion (25) of the tap (24), substantially facing away from the at least one first engagement surface (19), defines the at least one second engagement surface (21) on the coupling portion (15) of the driving and retraction member (9b).

9. The fixing means according to claim 8, wherein a groove or recess (27) for engaging the coupling portion (11), which is at the rear of the fixing member (9a) of the at least one pin (9), is defined peripherally about the outside of the tap (24) between the end surface (23) on the intermediate portion (16) of the driving and retraction member (9b) of the at least one pin (9) and the at least one second engagement surface (21) on the coupling portion (15) at the front of the driving and retraction member (9b).

10. The fixing means according to claim 4, wherein the thicker end part (25) on the tap (24) is formed by a substantially cylindrical or rod-like part.

11. The fixing means according to claim 4, wherein the thicker end part (25) on the tap (24) is formed by a substantially spherical part.

12. The fixing means according to claim 4, wherein the coupling portion (11) at the rear of the fixing member (9a) of the at least one pin (9) has an end surface (29) and a lateral groove or recess (30) in the coupling portion (11) for insertion therein of the tap (24) and the thicker part (25) on the free end of the tap (24) of the coupling portion (15) at the front of the driving and retraction member (9b) of the at least one pin (9).

13. The fixing means according to claim 12, wherein the lateral groove or recess (30) has a first width for insertion therein of the tap (24) and a second width for insertion therein of the thicker part (25) on the free end of the tap (24).

14. The fixing means according to claim 13, wherein the end surface (29) on the coupling portion (11) at the rear of the fixing member (9a) of the at least one pin (9) defines the at least one first engagement surface (20) on said coupling portion (11), and that a surface (32), facing substantially away from the at least one first engagement surface (20) and defining the second width of the groove or recess (30), defines the at least one second engagement surface (22) on said coupling portion (11).

15. The fixing means according to claim 13, wherein an end surface (33) in the groove or recess (30) in the coupling portion (11) at the rear of the fixing member (9a) of the at least one pin (9) defines the at least one first engagement surface (20) on said coupling portion (11), and that a surface (32), substantially facing the at least one first engagement surface (20) and defining the second width of the groove or recess (30), defines the at least one second engagement surface (22) on said coupling portion (11).

16. The fixing means according to claim 2, wherein the at least one pin (9) is displaced forward in the driving direction relative to the sleeve (2) until a stop surface (46) of the rear end portion (13) of the driving and retraction member (9b) is brought into engagement with the sleeve (2) at the opening of the rear end portion (4) of the sleeve (2).

17. The fixing means according to claim 16, wherein the driving and retraction member (9b) of the at least one pin (9) and the sleeve (2) are configured such that the at least one front end portion (10) of the fixing member (9a) of the at least one pin (9) is driven out as far as possible through the at least one opening (8) in the sleeve (2) when the stop surface (46) of the rear end portion (13) of the driving and retraction member (9b) is brought into engagement with the sleeve (2) at the opening of the rear end portion (4) of the sleeve (2).

18. The fixing means according to claim 16, wherein the stop surface (46) is for engagement with an end surface at the opening of the rear end portion (4) of the sleeve (2).

19. The fixing means according to claim 2, wherein the at least one pin (9) is displaced forward in the driving direction relative to the sleeve (2) until the rear end portion (13) with the seat (14) for a driving tool on the driving and retraction member (9b) of the at least one pin (9) is brought into engagement with a seat (45) for a driving tool at the opening of the rear end portion (4) of the sleeve (2).

20. The fixing means according to claim 19, wherein the driving and retraction member (9b) of the at least one pin (9) and the sleeve (2) are configured such that the at least one front end portion (10) of the fixing member (9a) of the at least one pin (9) is driven out as far as possible through the at least one opening (8) in the sleeve (2) when the rear end portion (13) with the seat (14) for a driving tool on the driving and retraction member (9b) is brought into engagement with the seat (45) for a driving tool at the opening of the rear end portion (4) of the sleeve (2).

21. The fixing means according to claim 19, wherein the rear end portion (13) with the seat (14) for a driving tool on the driving and retraction member (9b) of the at least one pin (9) is configured with a stop surface (46) for engagement with a bottom surface (47) of the seat (45) for a driving tool at the opening of the rear end portion (4) of the sleeve (2).

* * * * *